(12) United States Patent
Nelson

(10) Patent No.: US 7,954,230 B2
(45) Date of Patent: Jun. 7, 2011

(54) METHOD FOR MAKING SOOT SENSOR

(75) Inventor: Charles Scott Nelson, Fenton, MI (US)

(73) Assignee: Delphi Technologies, Inc., Troy, MI (US)

( * ) Notice: Subject to any disclaimer, the term of this patent is extended or adjusted under 35 U.S.C. 154(b) by 582 days.

(21) Appl. No.: 11/998,238

(22) Filed: Nov. 29, 2007

(65) Prior Publication Data

US 2009/0139081 A1    Jun. 4, 2009

(51) Int. Cl.
*H01C 7/02* (2006.01)
(52) U.S. Cl. ............. 29/612; 29/610.1; 29/613; 29/620
(58) Field of Classification Search ............. 29/611, 29/592.1, 610.1, 612, 613, 620; 338/22 R, 338/25, 34, 256
See application file for complete search history.

(56) References Cited

U.S. PATENT DOCUMENTS

| | | | |
|---|---|---|---|
| 6,482,650 B1 | 11/2002 | Kato et al. | |
| 2004/0202227 A1* | 10/2004 | Nelson et al. | 374/208 |
| 2005/0098433 A1* | 5/2005 | Gundel | 204/403.02 |
| 2006/0170015 A1* | 8/2006 | Wienand et al. | 257/254 |

FOREIGN PATENT DOCUMENTS

| | | |
|---|---|---|
| EP | 1814226 | 8/2007 |
| WO | 9203833 | 3/1992 |
| WO | 0125775 | 4/2001 |

OTHER PUBLICATIONS

EP Search Report dated Apr. 27, 2009.

* cited by examiner

*Primary Examiner* — Thiem Phan
(74) *Attorney, Agent, or Firm* — Jimmy L. Funke

(57) ABSTRACT

An ablating device is used to form a pattern into a sensing element pad of a soot sensor, with the pattern establishing two finger paths without electrical connection between them. The pattern can be formed through a protective layer on the sensing element pad before the sensing element pad is fired.

7 Claims, 4 Drawing Sheets

METHOD FOR MAKING SOOT SENSOR

I. FIELD OF THE INVENTION

The present invention relates generally to methods of making soot sensors for burners or engines.

II. BACKGROUND OF THE INVENTION

Soot sensors, used to measure particulate in, e.g., engine exhaust, typically can be established by simple resistive devices. Such a sensor typically consists of a non-conductive substrate, most often alumina, with a screen print pattern using a conductive material, often a precious metal in order to withstand the temperature of a co-fire (although co-fire may not be necessary). The opposite side of the substrate can bear a heater to heat the soot sensor when needed to remove excess soot.

The soot sensing portion of the element consists of two electrodes with inter-digitized "fingers" that maximizes a perimeter between the two electrodes. When soot from the exhaust lands on the sensor, the carbon makes a high resistance short between the electrodes, effectively lowering the resistance. The more the soot collects, the lower the resistance, and this resistance is measured as an indication of the amount of soot. If it is desired to clean off the soot from the element, the heater on the element is activated to clean off the element.

While the electrodes of a soot sensor must be exposed to the exhaust stream in order to work, they must also be protected from being abraded away from the exhaust gas. U.S. Pat. No. 7,280,028 and application Ser. No. 11/750,883, owned by the present assignee and incorporated herein by reference, discuss such protection.

As understood herein, it is desirable to establish as long of a path between the two electrodes as possible, because once the carbon shorts the path, the more connections that are made, the higher the signal. Further, as also recognized herein the shorter the distance between the paths, the higher the sensitivity of the signal. With these recognitions in mind, the invention herein is provided.

SUMMARY OF THE INVENTION

A method includes establishing an electrically conductive sensing element pad on a substrate with at least a sensing end portion of the pad being continuously solid. The method also includes forming a pattern in the sensing end portion of the pad and no other region of the pad using a laser or other ablating device.

The pad can include a conductive ink and the act of forming may be undertaken prior to firing the ink. A protective layer can be disposed on the pad prior to the act of forming, in which case the act of forming includes cutting the pattern into the protective layer and pad. Or, the ablating device may be used to form the pattern after firing the ink.

In non-limiting implementations the substrate can be laminated to a heater prior to cutting the pattern. Plural soot sensors may be formed as a single assembly and then separated from each other. In any case, the pad is electrically connected to a computer and uses the cut pattern to generate signals representative of soot.

In another aspect, a method for making a soot sensor for a vehicle includes establishing at least one electrically conductive sensing element pad on a non-conductive substrate, and using an ablating device to establish two separate inter-digitized fingers paths without electrical connection between the finger paths.

In still another aspect, a method for generating a signal representative of soot in an exhaust includes forming a soot sensor at least in part using an ablating device, disposing the soot sensor in an exhaust, and establishing communication between the soot sensor and a control module.

The details of the present invention, both as to its structure and operation, can best be understood in reference to the accompanying drawings, in which like reference numerals refer to like parts, and in which:

DETAILED DESCRIPTION OF THE PREFERRED EMBODIMENT

Figure 1:
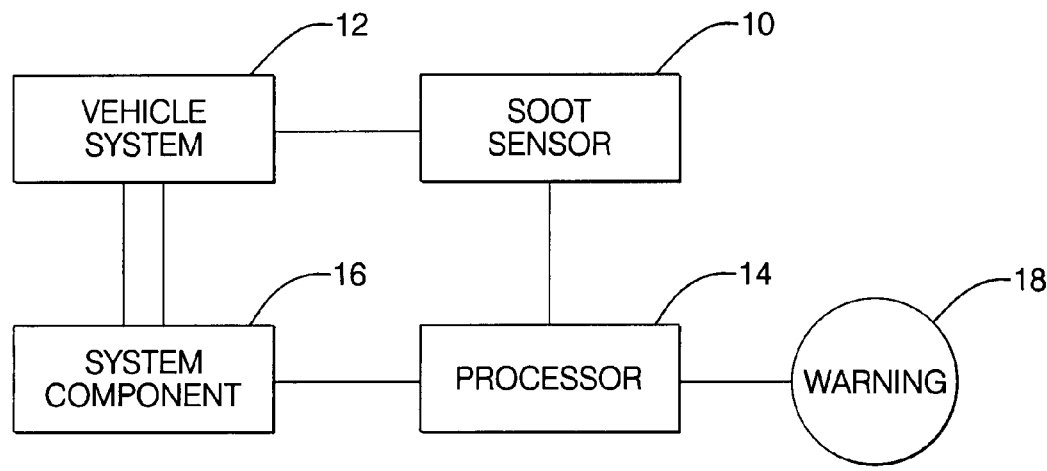
FIG. 1 is a block diagram of a non-limiting environment of the present invention.

FIG. 1 illustrates a soot sensor 10 that is in communication with a vehicle system 12, such as a vehicle exhaust system, to generate a signal representative of soot in the system 12. The signal may be sent (via appropriate processing circuitry and wired or wireless communication links) to a processor 14 such as a vehicle control module (ECM), with the processor 14 in response sending commands to a system component 16 such as a valve or the like that is part of the system 12, and/or with the processor 14 activating a warning lamp or speaker 18 to indicate high soot levels.

Figure 2:
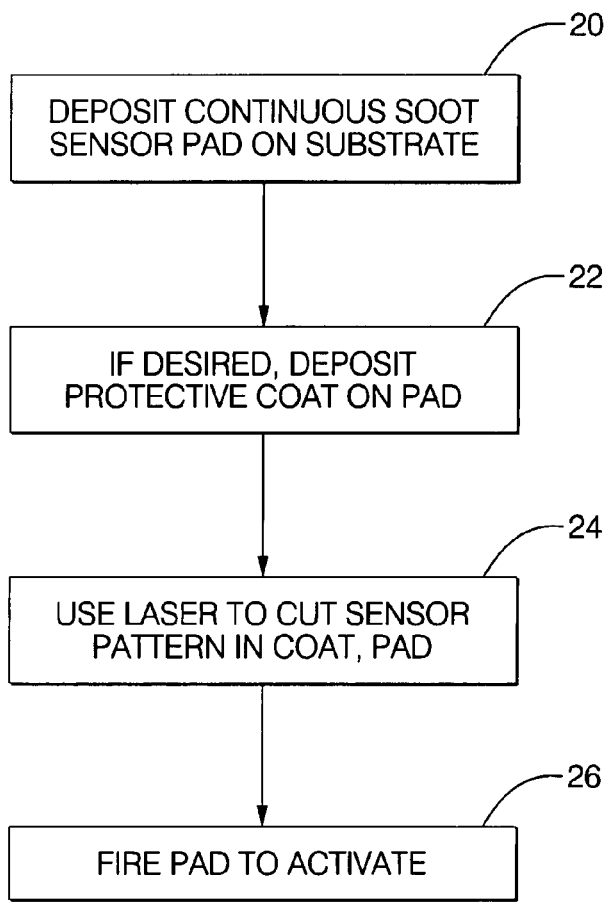
FIG. 2 is a flow chart showing steps of an exemplary non-limiting method of the invention.

Now referring to FIG. 2, at block 20 a pad made of electrically conductive material that will serve as the sensing element of the soot sensor 10 is deposited onto a substrate such as a pre-fired alumina substrate or a layer of high temperature ceramic co-fire (HTCC) tape. It is to be understood that a heater may be formed by, e.g., thick film screen printing on an opposite surface of the substrate prior to or after depositing the pad. The pad may be, e.g., conductive ink.

Optionally, at block 22 a protective layer of, e.g., alumina may be deposited over the pad by, e.g., screen printing. Or, the protective layer can be established later in the process if desired. At block 24 an ablating device is used to cut a pattern into a completely solid generally parallelepiped-shaped end of the pad (and, if included, protective layer) such that two separate winding or zig zag or inter-digitized fingers paths are made in the end of the pad without electrical connection between them. In non-limiting implementations the ablating device cuts a thin path, typically fourteen to thirty eight (14-38) microns, to separate the two conductive paths.

Ablating can take place before or after firing the ink, but as set forth herein preferably before firing. The protective coating likewise preferably is established before ablating to ensure contact between the soot and electrodes remains possible.

With greater specificity, the ablated pattern may be cut into the pad and substrate with the ink of the pad in the green, unfired state, because as understood herein the ink in this state is easier to ablate, thus requiring less power. Furthermore, cutting the pattern before firing the ink results in even smaller spacing between fingers in the final product owing to shrinkage during firing. And, ablating before firing the ink facilitates use of a protective coating that can be dyed so that it absorbs the heat better if using a laser. The laser can burn off slightly more protective layer than ink so that in the final product the soot can reach the electrodes easier.

Figure 3:
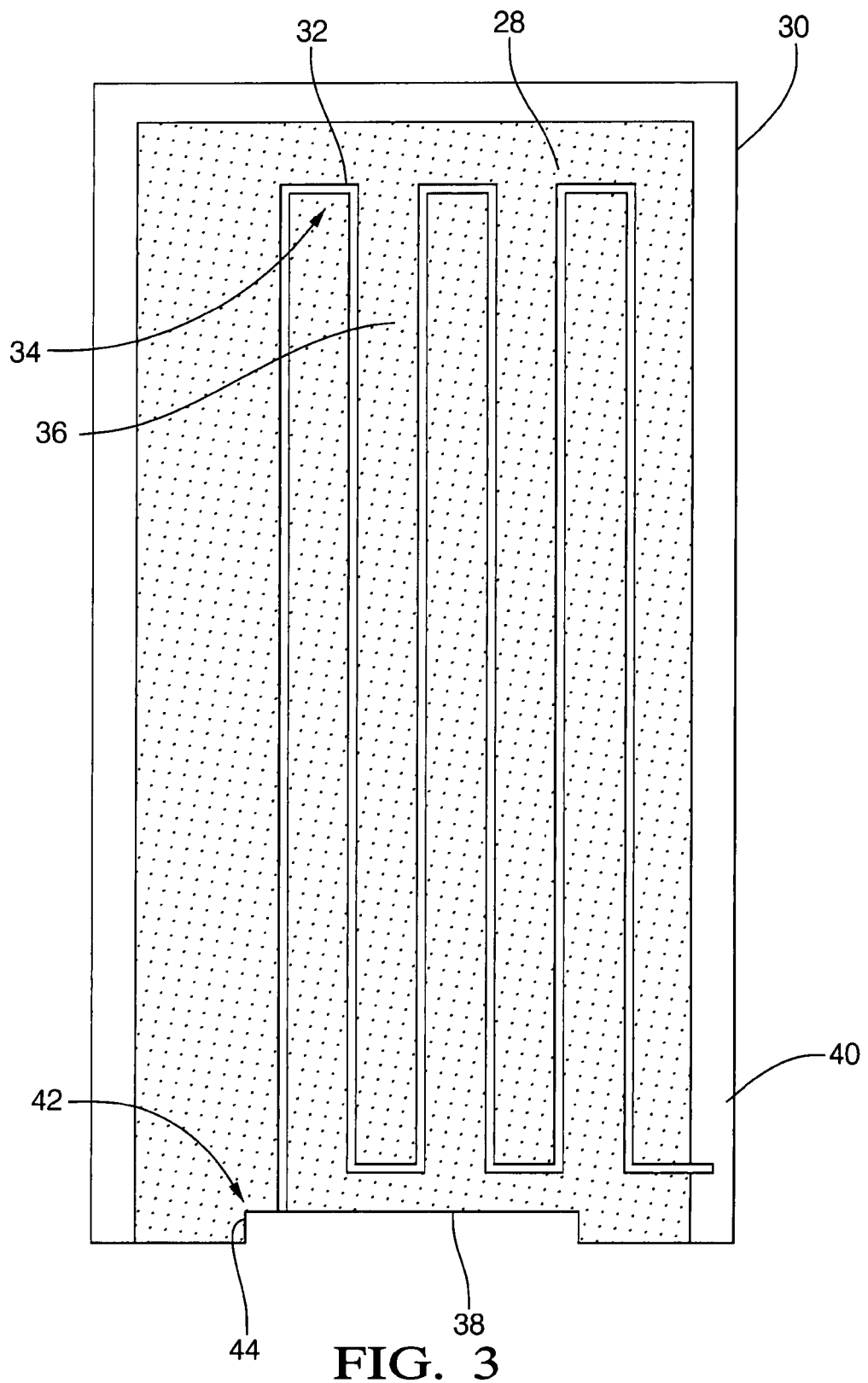
FIG. 3 is a top plan view of the sensing element end of a sensor made in accordance with present principles.

FIG. 3 shows a sensing element pad 28 on a substrate 30 after a pattern 32 has been cut into the sensing element pad 28 using an ablating device as described above. It will readily be appreciated that prior to ablating the portion of the sensing element pad 28 into which the pattern 32 is to be formed is a continuous solid parallelepiped-shaped layer. The pattern 32 establishes two separate winding or zig zag or inter-digitized fingers paths 34, 36 that are established without electrical connection between them, owing to the pattern 32. Each finger path 34, 36 is connected to a respective conductive lead 38, 40 as shown, with the leads 38, 40 being established by elongated legs of the sensing element pad 28 that extend away from the continuous area that bears the pattern 32. As shown at 42, the pattern 32 may begin at a location that is distanced from an edge 44 of the pad end of a conductive lead 38 to avoid tolerance stack up.

Figure 4:
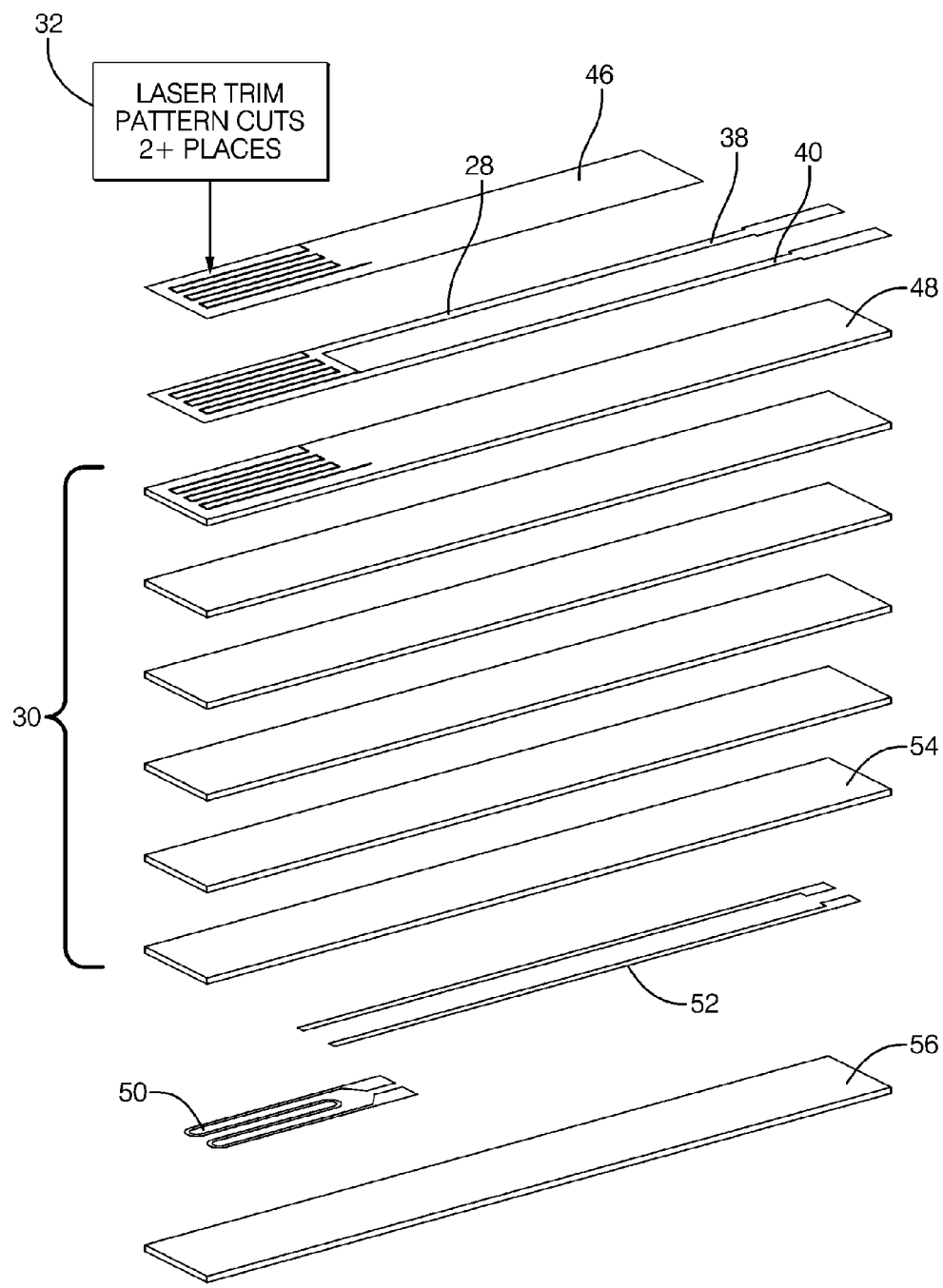
FIG. 4 is an exploded perspective view of a complete non-limiting soot sensor in accordance with present principles.

FIG. 4 shows an exploded view of a complete soot sensor 10. As shown, the sensing element pad 28 may be deposited onto a multi-layer substrate 30 made of, e.g., HTCC tape. A protective layer 46 may be on the sensing element pad 28 as shown, and the ablating device may cut the pattern 32 in the protective layer 46, sensing element pad 28, and even into the top layer 48 of the multi-layer substrate 30 as shown. A heater 50 with heater leads 52 may be deposited or formed on a bottom layer 54 of the substrate 30 and covered with its own heater protective layer 56. The layers shown in FIG. 4 are substantially flush with each other and coterminous with each other, except that the pad protective layer 46 might not extend all the way to the end of the electrode legs 38, 40 of the sensing element pad 28 as shown.

Figure 5A:
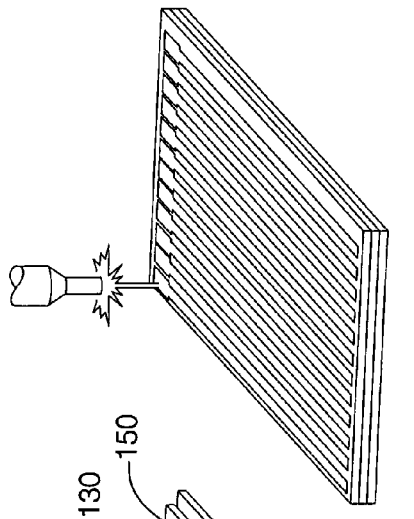
FIGS. 5A-5E are a sequence of views of a multi-sensor assembly to illustrate the steps shown in FIG. 2.
Figure 5B:
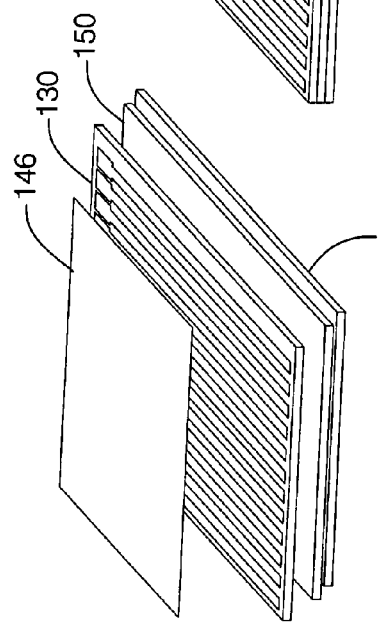
Figure 5C:
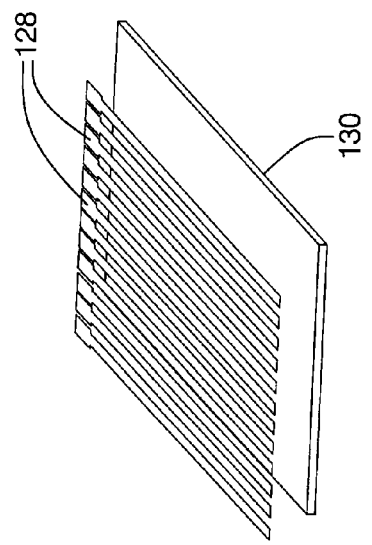
Figure 5D:
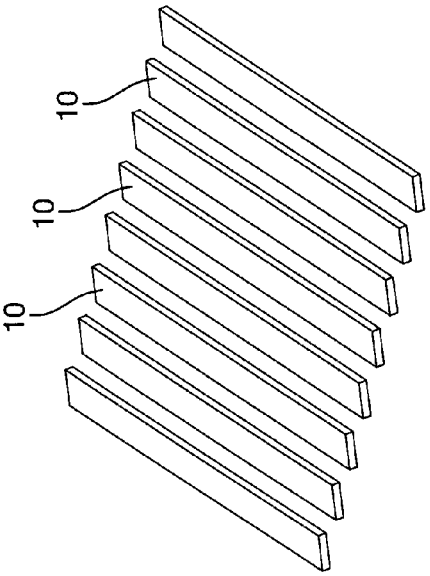
Figure 5E:

FIG. 5A illustrates that multiple soot sensors 10 may be made from a common assembly. Plural sensing element pads 128 may be deposited onto a common substrate 130 as shown in FIG. 5A, and then a sensor protective layer 146 oriented on the pads 128 with a heater layer 150 and heater protective layer 156 oriented under the substrate 130 as shown in FIG. 5B. The layers are laminated together and then as shown in FIG. 5C an ablating device is used to cut the above-discussed patterns into the parallelepiped-shaped sensing element ends of the sensing element pads 128. The individual soot sensors 10 are separated from each other as shown in FIG. 5D and then each is fired as indicated in FIG. 5E to activate the ink of the sensing elements.

The present process can be performed using thick film or thin film inks, with a heater on one side (which can have a protective coating) and with the sensing pad opposed thereto and then the pattern cut, with an optional protective top coat.

Or, the method can use HTCC tape with alumina layers, followed by heater print with alumina X layers on the heater for protection, followed by deposition of the continuous sensing pad by, e.g., printing, followed by depositing a protective layer on the pad, preferably an ink layer vs. tape layer so the ablating device does not have to cut through so much, followed by cutting of the desired electrode pattern.

Large debris or particles, which are not required by regulation to be detected, are prevented from shorting out the electrodes because they are larger than the width of the pattern cut.

One method of putting the protective coating on afterwards is pad printing on a relatively course ink that would not flow into the pattern cut. A pre-fired substrate can be used in lieu of green tape. A glass coating on top of the electrode may be used as long as it doesn't flow into the pattern-cut grooves. A pattern can be formed on both sides of the substrate and joined by vias through the substrate. Pattern cutting may be conducted prior to lamination.

While the particular METHOD FOR MAKING SOOT SENSOR is herein shown and described in detail, it is to be understood that the subject matter which is encompassed by the present invention is limited only by the claims.

What is claimed is:

1. A method for making a soot sensor comprising:
   establishing at least one electrically conductive sensing element pad on a non conductive substrate;
   disposing a protective layer on the element pad; and
   using an ablating device to cut a pattern into the protective layer and pad so as to establish two separate inter-digitized fingers paths in the pad without electrical connection between the finger paths and so as to leave a portion of the perimeter of the inter-digitized finger paths exposable to soot.

2. The method of claim 1, wherein a sensing end portion of the pad is continuously solid, and the method comprises:
   forming a pattern in the sensing end portion of the pad and no other region of the pad using an ablating device to establish the finger paths.

3. The method of claim 1, wherein the pad includes a conductive ink and the act of forming is undertaken prior to firing the ink.

4. The method of claim 1, wherein the pad includes a conductive ink and the act of using an ablating device is undertaken after firing the ink.

5. The method of claim 1, comprising laminating the substrate to a heater prior to the act of using an ablating device.

6. The method of claim 5, wherein plural soot sensors are formed as a single assembly and then separated from each other.

7. The method of claim 1, comprising electrically connecting the pad to a computer and using the pad to generate signals representative of a soot.

\* \* \* \* \*